(12) United States Patent
Park et al.

(10) Patent No.: US 8,898,890 B2
(45) Date of Patent: Dec. 2, 2014

(54) APPARATUS FOR MANUFACTURING A MULTICHANNEL ELECTRODE ARRAY FOR CRANIAL NERVE STIMULATION

(75) Inventors: Se-Ik Park, Gyeonggi-do (KR); Hoseung Lee, Gyeonggi-do (KR); Jung Min Lee, Gyeonggi-do (KR); Ho Yun, Gyeonggi-do (KR)

(73) Assignee: M.I.Tech Co., Ltd., Gyeonggi-do (KR)

( * ) Notice: Subject to any disclaimer, the term of this patent is extended or adjusted under 35 U.S.C. 154(b) by 166 days.

(21) Appl. No.: 13/583,413

(22) PCT Filed: Apr. 28, 2010

(86) PCT No.: PCT/KR2010/002701
§ 371 (c)(1),
(2), (4) Date: Sep. 7, 2012

(87) PCT Pub. No.: WO2011/111899
PCT Pub. Date: Sep. 15, 2011

(65) Prior Publication Data
US 2013/0000112 A1    Jan. 3, 2013

(30) Foreign Application Priority Data
Mar. 10, 2010 (KR) ........................ 10-2010-0021143

(51) Int. Cl.
*B23P 19/00* (2006.01)
*A61N 1/05* (2006.01)
*A61N 1/36* (2006.01)

(52) U.S. Cl.
CPC .......... *A61N 1/0529* (2013.01); *A61N 1/36021* (2013.01); *A61N 1/36025* (2013.01)

USPC .................... 29/746; 29/749; 29/754; 29/760

(58) Field of Classification Search
USPC ........... 29/746, 749, 752, 754, 760, 825, 874, 29/876; 219/69.12, 69.17
See application file for complete search history.

(56) References Cited

U.S. PATENT DOCUMENTS

| 4,530,471 A | * | 7/1985 | Inoue .......................... 242/420.1 |
| 4,936,306 A | | 6/1990 | Doty |
| 5,753,879 A | * | 5/1998 | Yang et al. ................. 219/69.12 |
| 6,747,236 B1 | | 6/2004 | Magara et al. |
| 2006/0184209 A1 | | 8/2006 | John et al. |

FOREIGN PATENT DOCUMENTS

| JP | 2004358078 | 12/2004 |
| JP | 2007325652 | 12/2007 |

* cited by examiner

*Primary Examiner* — Thiem Phan
(74) *Attorney, Agent, or Firm* — Bacon & Thomas, PLLC

(57) ABSTRACT

According to the present invention, an apparatus for manufacturing a multichannel electrode array for cranial nerve stimulation comprises: an electrode support supporting a plurality of electric wires, and having a plurality of platinum rings inserted therein; a frame member including a base, a pair of vertical frames, and a horizontal frame to fix the electrode support; a rotating member into the center of which the electrode support is inserted, and which rotates such that electric wires are twisted, pair by pair, at the electrode support so as to form a grid, when bobbins that are wound with the electric wires slide; an elevating plate rotatably and slidably supporting the rotating member; and a pair of left-side and right-side control units and which rotate the rotating member such that the rotating member slides along a length equal to that the grid.

9 Claims, 9 Drawing Sheets

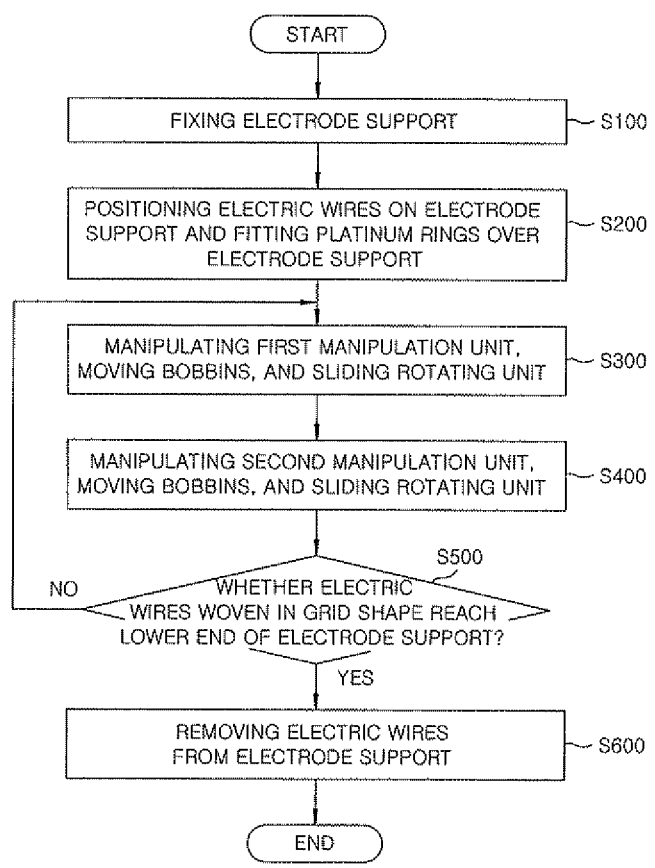

APPARATUS FOR MANUFACTURING A MULTICHANNEL ELECTRODE ARRAY FOR CRANIAL NERVE STIMULATION

TECHNICAL HELD

The present invention relates, in general, to apparatuses and methods for manufacturing multichannel electrode arrays for providing cranial nerve stimulation which are used in next-generation deep brain stimulators for treating dyskinesia or pains and, more particularly, to an apparatus and method for manufacturing a multichannel electrode array which is formed by twisting electric wires to form a grid so that it can withstand force or impact applied to a stimulation electrode when manipulating the stimulation electrode for a deep brain stimulator which is transplanted in a head cavity to stimulate a specific structure of a brain.

BACKGROUND ART

As is well known to those skilled in this art, Parkinson's disease is a degenerative brain disorder of the nonvascular system which is the next most common after senile dementia. This disease is very prevalent among the elderly. As the elderly population increases, the rate of incidence of this disease is concomitantly increasing. Although the pathogenesis of Parkinson's disease has not yet been clearly determined, a lack of dopamine which is a kind of neurotransmitter is known to be an immediate cause of this disease. This causes different kinds of dyskinesia such as hand tremors or bradykinesia. Up to now, a fundamental therapy has not yet been discovered.

Methods of treating Parkinson's disease, for example, include drug treatments for supplementing insufficient dopamine, and surgery which completely removes a brain structure that is malfunctioning attributable to the lack of dopamine. Recently, a method for treating dyskinesia was disclosed, in which fine thin electrodes are inserted into deep brain structures such as the thalamus, globus pallidus and subthalamus and then electric stimulation is applied thereto. An apparatus that is used in this method is called a deep brain stimulator (DBS). A representative example of the DBS was proposed in US patent No. 2006/0184209, which was filed by Constance M. John, etc. on Aug. 17, 2006 and entitled "DEVICE FOR BRAIN STIMULATION USING RF ENERGY HARVESTING".

Advantages of this deep brain stimulation method are that compared to drub treatment or surgery, the remedial effects are superior, the risk of brain damage is low, and it is not required to remove brain tissues. Therefore, this method is receiving much attention as a new therapy. Improvements in relieving the symptoms of Parkinson's disease using such a DBS are comparatively superior and satisfactory to 90%. The use of DBS was permitted by the FDA (Food and Drug Administration). According to a report of the NIH (National Institutes of Health), more than 2000 patients underwent a DBS transplant operation.

However, DBSs that are being transplanted have to overcome problems of a limited battery life which causes frequent replacement of the DBS, its large size making the surgery complex, etc. Next-generation DBSs that overcome these problems are being actively developed. To prove the effectiveness of developed DBSs and increase the range of application of the DBSs (e.g. to apply the DBSs to treatments for pain, epilepsy, etc.), animal testing (using animals, only one half of the brain to which a Parkinson's disease lesion is applied) is proceeding.

In the animal tests using the DBSs, because animal models must be biologically safe, the DBSs must have no effect on living bodies, stimulation electrodes or electric stimulation must not cause brain cell destruction, and the material used to make the stimulation electrodes must be biocompatible. To conduct deep brain stimulation therapy, the precise location of a lesion in the deep structure of the brain must be determined. For this, images using MRI (magnetic resonance imaging) and fine electrodes are used in combination, markedly enhancing the degree of precision of location setting and the surgery.

A fine electrode which can record nerve signals from the deep structures of the brain is formed such that the end thereof is sharp. Further, in the metal electrode that is used, all parts of it except for a nerve signal measuring part are insulated. Such a fine metal electrode is manufactured in such a way that an insulation film is applied to a metal wire that has a pointed end and then a portion of the insulation film that corresponds to the pointed end is removed so that the metal of the nerve signal measuring part is exposed to the outside from the insulation film. However, because the deep brain stimulation therapy aims to measure nerve signals from a single nerve cell, only about several μm of the metal of the nerve signal measuring part must be exposed to the outside. Depending on the purpose, in other words, whether it is for blood vessels or spines, a plurality of platinum rings must be provided at regular intervals.

In the above-stated conventional fine electrodes, the material of the electrode is platinum, it is very thin, and several electrodes are longitudinally arranged in a line. Therefore, the electrode basically has low tensile strength. Thus, if a force or impact is longitudinally applied to the electrode, it easily snaps.

To overcome these problems, electrodes may be manufactured in such a way that they are twisted to form a helical shape. However, in this case, there is a likelihood of the electrodes becoming tangled. If the electrodes are tangled, the tangled portion also easily snaps when force is longitudinally applied thereto.

DISCLOSURE

Technical Problem

Accordingly, the present invention has been made keeping in mind the above problems occurring in the prior art, and an object of the present invention is to provide a apparatus and method for manufacturing a multichannel electrode array for cranial nerve stimulation which has a grid connection part provided on an electrode so that the electrode can withstand an unforeseen force or impact applied thereto.

Technical Solution

In accordance with an aspect of the present invention, there is provided an apparatus for manufacturing a multichannel electrode array for cranial nerve stimulation, comprising: an electrode support supporting a plurality of electric wires, with a plurality of platinum rings fitted over the electrode support; a frame unit fixing the electrode support; a rotating unit comprising upper and lower plates coupled to upper and lower ends of a rotating shaft, the rotating unit being rotated in such a way that when bobbins around which the respective electric wires that are supported by the electrode support are wound slide on the upper plate, the electric wires are twisted pair by pair on the electrode support; an elevating plate rotatably and slidably supporting the rotating unit; and a pair of manipulation units rotating the rotating unit such that the rotating unit slides for a length of the grid.

In accordance with another aspect of the present invention, there is provided a method of manufacturing a multichannel electrode array for cranial nerve stimulation using the apparatus according to any one of claims 1 through 9, comprising: fixing the electrode support; positioning the electric wires on the electrode support, and fitting the platinum rings over the electrode support; manipulating the first manipulation unit so that the inner bobbins that have been disposed on the upper inner plate are moved outwards, and the outer bobbins are moved inwards, and sliding the rotating unit to a lower platinum ring; manipulating the second manipulation unit so that the bobbins that have been disposed on the upper outer plate are moved onto the upper inner plate, and the bobbins that have been disposed on the upper inner plate are moved onto the upper outer plate, and sliding the rotating unit to a subsequent lower platinum ring; controlling the first and second manipulation units until the electric wires woven in a grid shape reach the lower end of the electrode support; and removing the electric wires from the fixed electrode support.

Advantageous Effects

In the present invention, four electric wires are vertically supported, and left and right wires and front and rear wires are alternately rotated and twisted in a grid shape pair by pair while moving downwards, thus forming a multichannel electrode array. Therefore, the multichannel electrode array can withstand even unforeseen force or impact applied thereto.

BRIEF DESCRIPTION OF THE DRAWINGS

FIG. 9 is a flowchart of a process of manufacturing the multichannel electrode array for cranial nerve stimulation according to the present invention.

BEST MODE FOR THE INVENTION

Hereinafter, the operation of an embodiment of the present invention will be described in detail with reference to the drawings.

Figure 1:
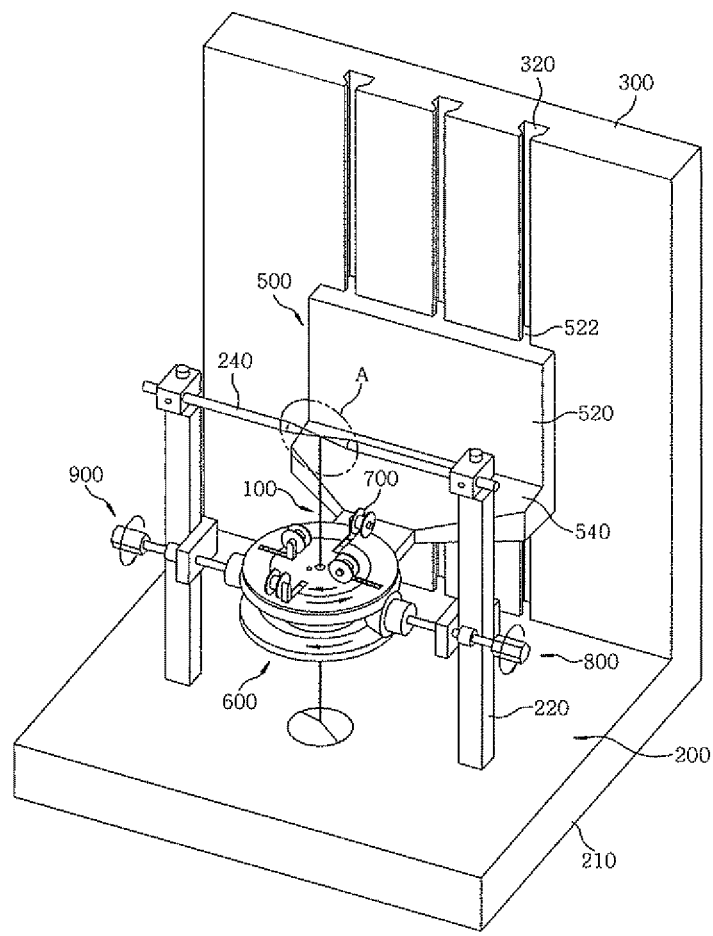
FIG. 1 is a schematic perspective view illustrating an apparatus for manufacturing a multichannel electrode array for cranial nerve stimulation which is used in a deep brain stimulator, according to an embodiment of the present invention.

FIG. 1 is a schematic perspective view illustrating an apparatus for manufacturing a multichannel electrode array for cranial nerve stimulation according to the embodiment of the present invention.

As shown in the drawing, the apparatus for manufacturing the multichannel electrode array for cranial nerve stimulation according to the present invention includes an electrode support 100, a frame unit 200, a rotating unit 600, an elevating plate 500 and a pair of left and right manipulation units 800 and 900. The electrode support 100 supports a plurality of electric wires. A plurality of platinum rings are fitted over the electrode support 100. The frame unit 200 includes a base 210, a pair of vertical frames 220 and a horizontal frame 240 and fixes the electrode support 100. The electrode support 100 is inserted into a central portion of the rotating unit 600. The rotating unit 600 rotates in such a way that when bobbins 700, around each of which an electric wire is wound, slide, the electric wires are twisted pair by pair on the electrode support 100 to form a grid. The elevating plate 500 rotatably and slidably supports the rotating unit 600. The left and right manipulation units 800 and 90° rotate the rotating unit 600 and slide it by a length of the formed grid.

Figure 2:
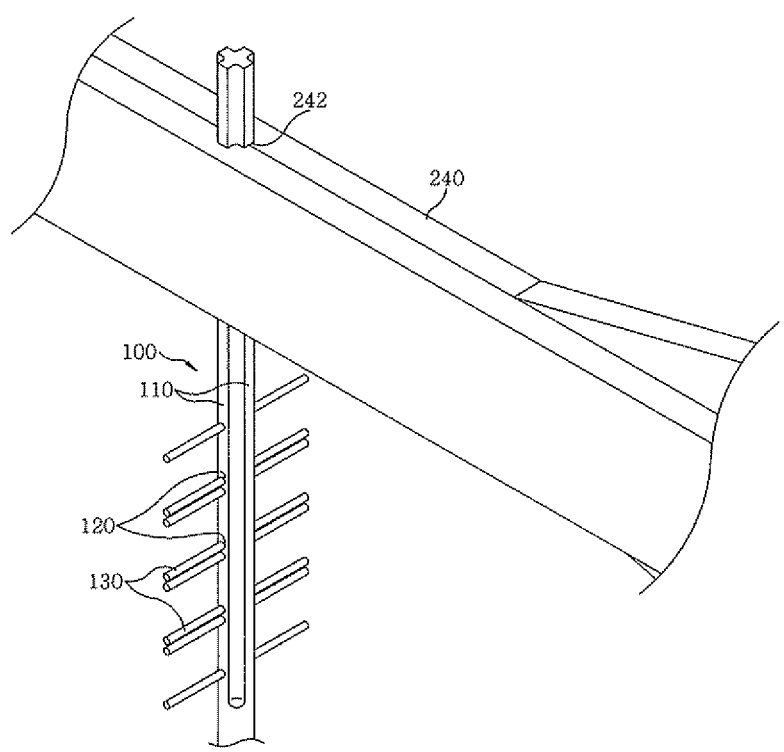
FIG. 2 is an enlarged view of the circled portion A of FIG. 1 that illustrates an electrode support fixed to a horizontal frame of FIG. 1.
Figure 3:
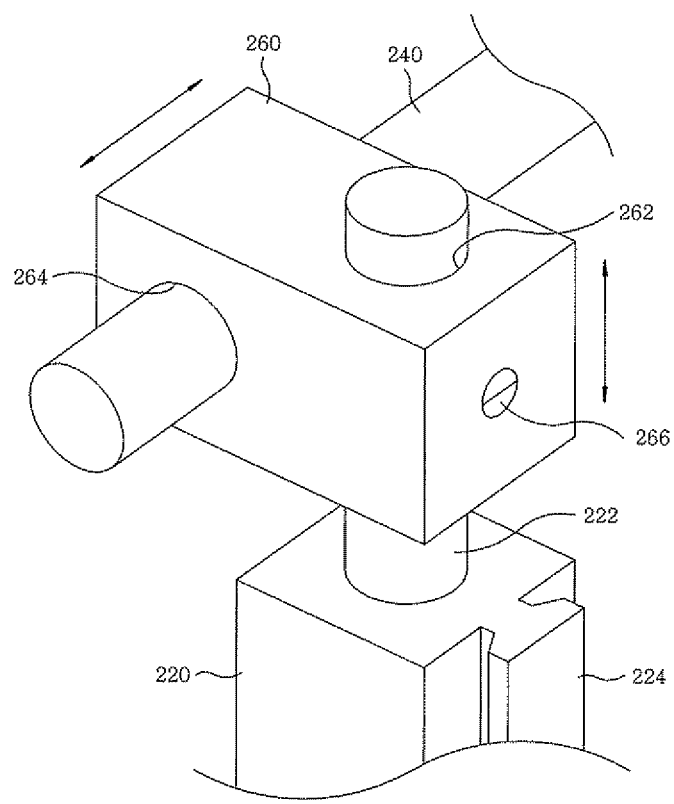
FIG. 3 is an enlarged view showing the construction of an upper end of a rear surface of a vertical frame of FIG. 1.

FIG. 2 is an enlarged view of the circled portion A of FIG. 1 that illustrates the electrode support fixed to the horizontal frame of FIG. 1. FIG. 3 is an enlarged view showing the construction of an upper end of a rear surface of the vertical frame of FIG. 1.

Referring to FIGS. 2 and 3, to insert electric wires into the electrode support 100 and attach a plurality of platinum rings around it at predetermined intervals, four wire positioning grooves 110 are formed at regular intervals around the electrode support 100 and longitudinally extend a predetermined length. Furthermore, the electrode support 100 further has a plurality of ring fastening holes 120 which are formed at intervals corresponding to the platinum rings to be attached, and fastening pins 130 which are fitted into the respective ring fastening holes 120. A first end of the electrode support 100 is inserted into an insert hole 212 of the base 210. A second end of the electrode support 100 is inserted into a support coupling hole 242 of the horizontal frame 240 after passing through a through hole 654 (refer to FIG. 4) of the rotating unit 600. The ring fastening holes 120 comprises uppermost and lowermost ring fastening holes which are respectively formed at upper and lower positions in the electrode support 100 below the horizontal frame, and two ring fastening holes which are formed at each of several proportions in the electrode support 100 between the uppermost and lowermost ring fastening holes to keep distances between the platinum rings. The distance between the ring fastening holes 120 and the number of ring fastening holes can be changed depending on the kind of the electrode.

A height adjustment rod 222 is disposed, so as to be movable vertically, in each of the vertical frames 220 of the frame unit 200 which are provided upright on the base 210 at positions spaced apart from each other by a predetermined distance. A height-adjustment-rod-coupling hole 262 is vertically formed in each connection member 260 so that the height adjustment rod 222 is coupled thereto by the height-adjustment-rod-coupling hole 262. A horizontal-frame-coupling hole 264 to which the horizontal frame 240 is coupled is formed in each connection member 260. The height adjustment rod 222 that is inserted into the coupling hole 262 is releasably fixed by an adjustment screw 266. The height of the horizontal frame 240 that is inserted in the opposite connection members 260 provided on the upper ends of the vertical frames 220 can be adjusted by vertically moving the connection members 260. A guide protrusion 224 is provided on a rear surface of each vertical frame 220. The horizontal frame 240 is also releasably fixed by adjustment screws so that the position thereof can be adjusted to the left or right, although this is not shown in detail in FIG. 3.

Figure 4:
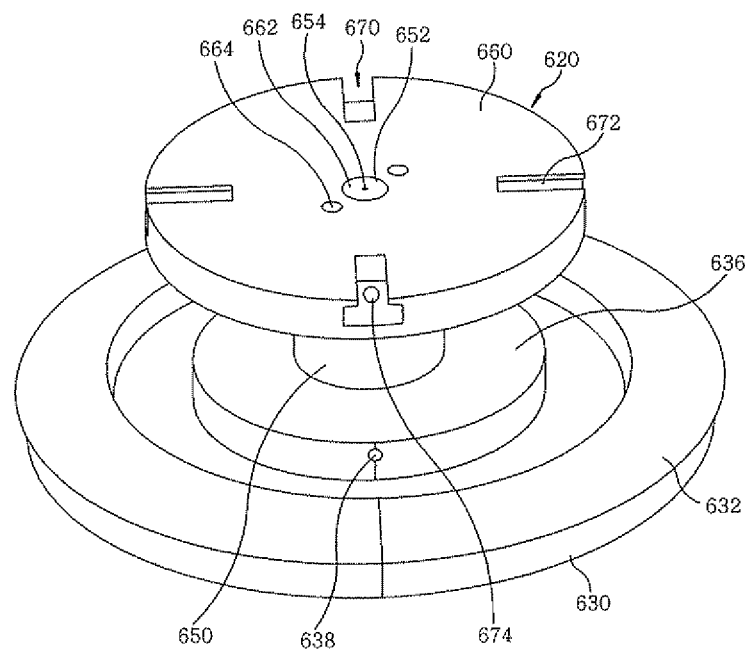
FIG. 4 is a perspective view illustrating a rotating member of FIG. 1.
Figure 5:
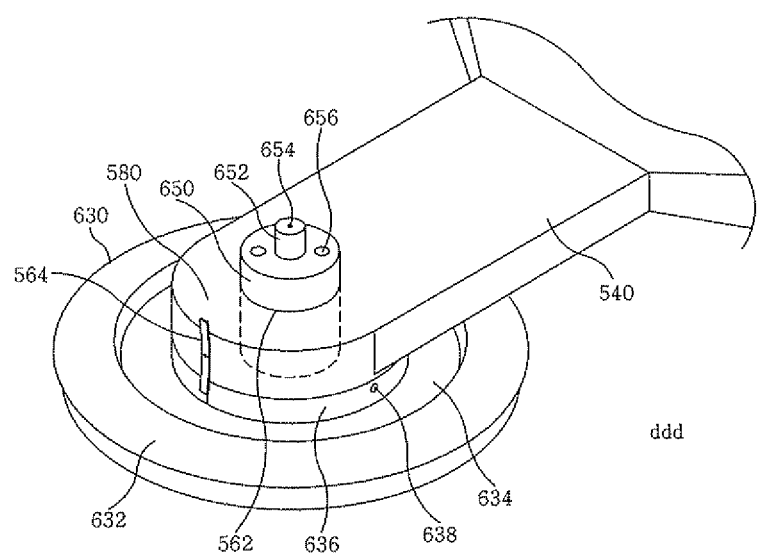
FIG. 5 is a perspective view illustrating the rotating unit of FIG. 4 that is coupled to a semicircular coupling part of a horizontal support unit of a sliding plate after an upper inner plate has been removed from the rotating unit.

FIG. 4 illustrates the rotating unit of FIG. 1. FIG. 5 illustrates the rotating unit of FIG. 4 that is coupled to a semicircular coupling part of a horizontal support unit of a sliding plate after an upper inner plate has been removed from the rotating unit FIG. 6 shows bobbins coupled to the upper inner plate and an upper outer plate of the rotating unit of FIG. 4.

Figure 6:
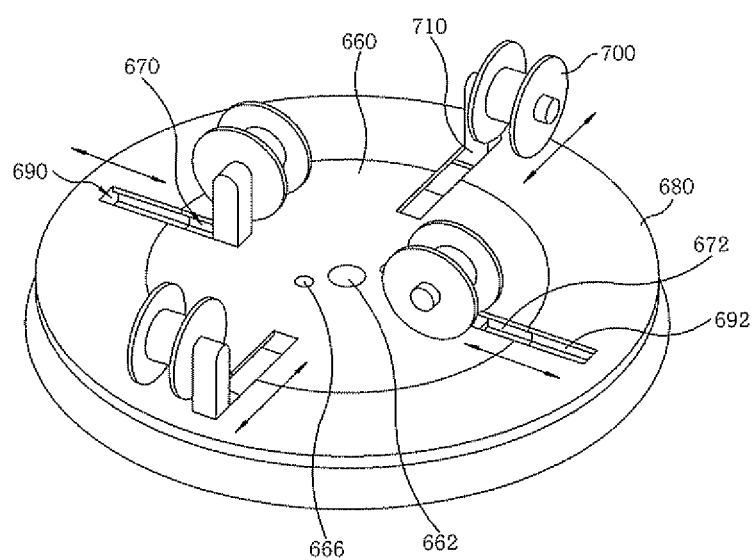
FIG. 6 is a perspective view showing bobbins coupled to the upper inner plate and an upper outer plate of the rotating unit of FIG. 4.

As shown in FIGS. 4 through 6, the rotating unit 600 includes a rotating shaft 650, an upper pinner plate 660 and a lower plate 630 which are respectively coupled to upper and lower ends of the rotating shaft 650, and an upper outer plate 680 which is rotatably coupled to an outer surface of the upper inner plate 660. The through hole 654 into which the electrode support 100 is inserted is formed in the central portion of the rotating shaft 650. A shaft coupling protrusion 652 which has screw coupling holes 656 is provided around the through hole 654. To correspond to this, a coupling hole 662, into which the shaft coupling protrusion 652 is inserted, and a screw coupling hole 664 is formed in the upper inner plate 660. A gear 632 is provided on the lower plate 630. A gear (not shown) that corresponds to the gear 632 is provided on the upper outer plate 680. An upper shaft flange 640 (refer to FIG. 7) and a lower shaft flange 636 are provided in the upper inner plate 660 and the lower plate 630 coaxially with the rotating shaft 650. Guide units 670 and 690 that correspond to each other are respectively formed in the upper inner plate 660 and the upper outer plate 680 so that bobbin support members 710 which support the respective bobbins 700 slide along the corresponding guide units 670 and 690. The guide units 670 and 690 respectively have guide slots 672 and 692 which communicate with each other. Ball seating depressions 674 and 694 are respectively formed in bottoms of the guide slots 672 and 692 so that the bobbin support members 710 can smoothly slide.

Two of the bobbins 700 are disposed in the corresponding guide units 670 of the upper inner plate 660, and the other two are disposed in the corresponding guide units 690 of the upper outer plate 680, and vice versa.

Figure 7:
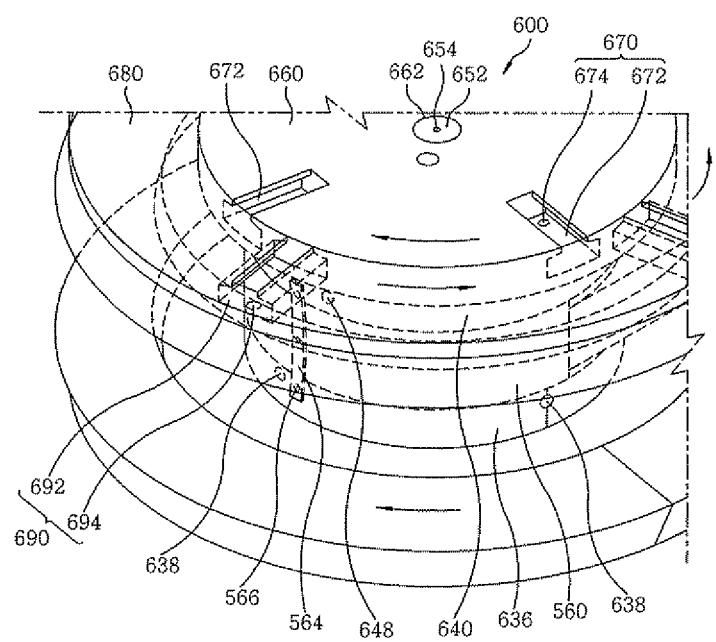
FIG. 7 is a partial perspective view showing the operation of rotating the rotating unit of FIG. 4.

Referring to FIGS. 1, 5 and 7, the elevating plate 500 includes on a first end thereof a rotating-unit-coupling part 540 which horizontally extends and is coupled to the rotating shaft 650 of the rotating unit 600. The elevating plate 500 further includes on a second end thereof a sliding-plate-coupling part 520 which has coupling protrusions 522. The coupling protrusions 522 are inserted into respective sliding slots 320 which are longitudinally formed in a sliding plate 300 so that the vertical movement of the sliding-plate-coupling part 520 is guided by the coupling protrusions 522 and the sliding slots 320. A semicircular shelf part 580 is provided on a front end of the rotating-unit-coupling part 540. The rotating shaft 650 of the rotating unit 600 is inserted into the semicircular shelf part 580. A rotation indication member 564 is attached to the semicircular shelf part 580. Protrusions 566 are provided on upper and lower ends of the rotation indication member 564. Four indication depressions 648, 638 are formed in each of the upper and lower shaft flanges 640 and 636 of the rotating unit 600 at positions spaced apart from each other at regular intervals of 90° so that the protrusions 566 of the rotation indication member 564 are inserted into the corresponding indication depressions 648 and 638.

Figure 8:
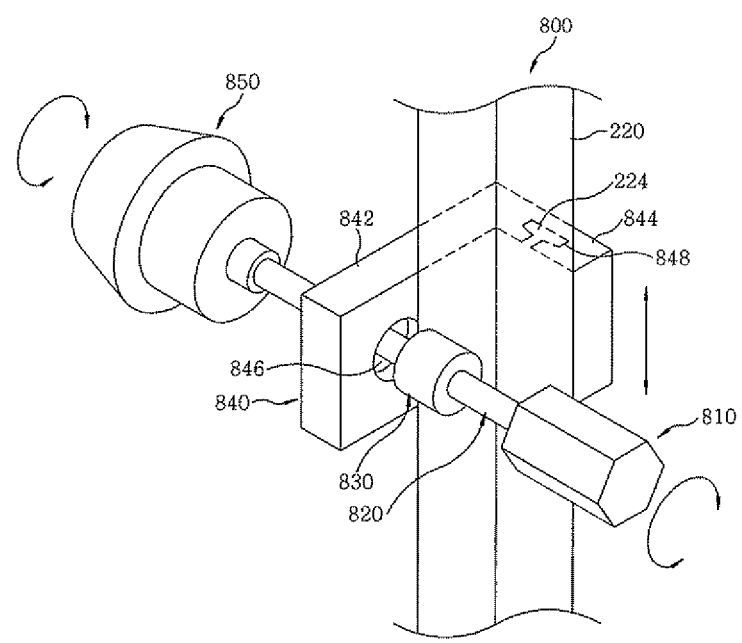
FIG. 8 is a perspective view illustrating in detail one of the manipulation units of FIG. 1.

Referring to FIGS. 1 and 8, the rotating unit 600 is rotated by the first and second manipulation units 800 and 900 coupled thereto and is moved upwards or downwards by the elevating plate 500. The first and second manipulation units 800 and 900 have the same construction. Only the first manipulation unit 800 will be explained.

The first manipulation unit 800 includes a conical geared member 850, a rotating shaft 820, a sliding member 840 and a handle 810. The conical geared member 850 engages with the gears of the upper outer plate 680 and the lower plate 630 of the rotating unit 600. The rotating shaft 820 is coupled to the geared member 850. The sliding member 840 is bent in an approximately "L" shape, is coupled to the rotating shaft 820, and is provided so as to be vertically movable along the vertical frame 220 of the frame unit 200. The handle 810 is connected to the rotating shaft 850. The sliding member 840 includes a shaft coupling part 842 which has a shaft hole 846 in which the rotating shaft 850 is disposed, and a frame coupling part 844 which extends perpendicularly from the vertical frame 220. A guide protrusion 224 of the vertical frame 220 is inserted into a guide groove 848 formed in the frame coupling part 844. A gear 830 is provided on the rotating shaft 820 so that the gear 830 comes into contact with a support surface of the vertical frame 220 that is opposite the guide protrusion 224. When the handle 810 rotates in a clockwise or counterclockwise direction, the rotating force of the handle 810 is transmitted to the vertical frame 220 by the gear. Then the sliding member 840 moves upwards or downwards along the vertical frame 220 by the same degree as the handle 810 is rotated by.

The conical geared member 850 engages both with the gear (not shown) formed on the upper outer plate 680 of the rotating unit 600 and with the gear 632 formed on the lower plate 630 in the same manner as that of bevel gears. Therefore, the upper inner plate 660 rotates in a direction opposite those of the upper outer plate 680 and the lower plate 630 so that after the rotation indication members 564 are completely coupled to the corresponding indication depressions 638 and 648, the two bobbins 700 that have been disposed on the upper inner plate 660 slide onto the upper outer plate 680 while the bobbins 700 that have been disposed on the upper outer plate 680 slide onto the upper inner plate 680.

That is, as shown in FIG. 8, if the handle 810 of the first manipulation unit 800 rotates inwards, the upper outer plate 680 of the rotating unit 600 rotates in a counterclockwise direction, and the lower plate 630 and the upper inner plate 660 rotate in a clockwise direction. When the upper inner plate 660 and the lower plate 630 have rotated by 90°, the indication protrusions 566 of the rotation indication member 564 are inserted into the corresponding indication depressions 648 and 638 formed in the upper and lower shaft flanges 640 and 636. Then, the bobbins 700 that have been disposed on the upper inner plate 660 are moved to the upper outer plate 680 along the guide grooves 672 by the left and right bobbin support members 710 of the bobbins 700 which are disposed in the guide units 670 of the upper inner plate 660. Further, the bobbins 700 that have been disposed on the upper outer plate 680 move onto the upper inner plate 660. Thereby, the electric wires that have been wound around the bobbins 700 are twisted on the electrode support 100 to form a grid. Simultaneously, the rotating unit 600 slides downwards along the vertical frame 200 by a predetermined pitch.

Subsequently, as shown in FIG. 8, if the handle 810 of the second manipulation unit 90° rotates inwards, contrary to the above, the upper outer plate 680 rotates in the clockwise direction, and the lower plate 630 and the upper inner plate 660 rotate in the counterclockwise direction. Thereby, the electric wires that have been wound around the bobbin 700 are twisted on the electrode support 100 to form a grid.

A process of manufacturing the multichannel electrode array for cranial nerve stimulation of the present invention having the above-mentioned construction will be explained with reference to FIG. 9.

First, at step S100, the height adjustment rods 222 of the vertical frames 220 and the horizontal frames 240 are adjusted so that the electrode support 100 is set at a correct fixed position. The electrode support 100 is inserted into the support coupling hole 242 of the horizontal frame 240 and the through hole 654 of the rotating unit 600 and fixed to the insert hole 212 of the base 210.

Thereafter, at step S200, the electric wires are positioned in the wire positioning grooves 110 of the fixed electrode support 100, and one fastening pin 130 is inserted into the ring fastening hole 120 that is disposed at the lowermost position. Subsequently, a platinum ring is fitted over the electrode support 100 and is resistance-welded to the platinum electric wires. Thereafter, another fastening pin 130 is inserted into the ring fastening hole 120 that is disposed just above the lowermost ring fastening hole 120. A second platinum ring is fitted over the electrode support 100. In the same manner, all the platinum rings are successively fitted over the electrode support 100 until the uppermost ring fastening hole 120.

At step S300, the handle 810 of the first manipulation unit 800 is rotated inwards until the indication protrusions 566 of the rotation indication member 564 are inserted into the indication depressions 648 and 638 formed in the upper and lower shaft flanges 640 and 636 of the rotating unit 600. Subsequently, the bobbins 700 that have been in the guide units 670 of the upper inner plate 660 are moved to the guide units 690 of the upper outer plate 680, and the bobbins 700 that have been in the guide units 690 of the upper outer plate 680 are moved to the guide units 670 of the upper inner plate 660.

Furthermore, at step S400, the handle 810 of the second manipulation unit 900 is rotated inwards until the indication protrusions 566 of the rotation indication member 564 are inserted into the corresponding indication depressions 648 and 638 formed in the upper and lower shaft flanges 640 and 636 of the rotating unit 600. Subsequently, the bobbins 700 that have been in the guide units 670 of the upper inner plate 660 are moved to the guide units 690 of the upper outer plate 680, and the bobbins 700 that have been in the guide units 690 of the upper outer plate 680 are moved to the guide units 670 of the upper inner plate 660.

At step S500, it is determined whether the electric wires woven in a grid shape reach the lower end of the electrode support 100. At step S600, if the electric wires woven in a grid shape do not reach the lower end of the electrode support, steps S300 and S400 are conducted. If the electric wires woven in a grid shape reach the lower end of the electrode support, the electric wires are removed from the electrode support 100 that have been inserted in the horizontal frame 240, thus completing the process of manufacturing the multichannel electrode array.

Although the preferred embodiment of the apparatus and method for manufacturing multichannel electrode array for cranial nerve stimulation according to the present invention has been disclosed for illustrative purposes, the present invention is not limited to the embodiment, and those skilled in the art will appreciate that various modifications, additions and substitutions are possible, without departing from the scope and spirit of the invention as disclosed in the accompanying claims.

The invention claimed is:

1. An apparatus for manufacturing a multichannel electrode array for cranial nerve stimulation, comprising:

an electrode support supporting a plurality of electric wires, with a plurality of platinum rings fitted over the electrode support;

a frame unit fixing the electrode support;

a rotating unit comprising upper and lower plates coupled to upper and lower ends of a rotating shaft, the rotating unit being rotated in such a way that when bobbins around which the respective electric wires that are supported by the electrode support are wound slide on the upper plate, the electric wires are twisted pair by pair on the electrode support;

an elevating plate rotatably and slidably supporting the rotating unit; and a pair of manipulation units rotating the rotating unit such that the rotating unit slides for a length of the grid.

2. The apparatus for manufacturing the multichannel electrode array for cranial nerve stimulation according to claim 1, wherein the electrode support has:

wire positioning grooves longitudinally formed in the electrode support at regular intervals so that the electric wires are inserted into the wire positioning grooves;

ring fastening holes formed to position the fitted platinum rings at regular intervals;

fastening pins inserted into the respective ring fastening holes.

3. The apparatus for manufacturing the multichannel electrode array for cranial nerve stimulation according to claim 1, wherein the frame unit comprises:

a base having an insert hole into which the electrode support is inserted;

a pair of vertical frames provided upright on the base at positions spaced apart from each other by a predetermined distance; and a horizontal frame coupled to the vertical frames by connection members.

4. The apparatus for manufacturing the multichannel electrode array for cranial nerve stimulation according to claim 1, wherein the rotating unit comprises:

the rotating shaft;

upper and lower shaft flanges respectively fitted over the upper and lower ends of the rotating shaft;

the upper plate coupled to the upper end of the rotating shaft, the upper plate comprising an inner plate and an outer plate; and the lower plate coupled to the lower end of the rotating shaft, wherein a gear provided on the upper inner plate, and a gear corresponding to the gear of the upper inner plate is provided on the lower plate, and guide grooves are formed in the upper inner and outer plates so that the bobbins slide along the guide grooves.

5. The apparatus for manufacturing the multichannel electrode array for cranial nerve stimulation according to claim 4, further comprising:

a sliding plate, with a sliding slot formed longitudinally in the sliding plate so that the elevating plate is coupled to the sliding plate by the sliding slot; and an upper shaft flange provided in the upper inner plate and the lower plate coaxially with the rotating shaft of the rotating unit;

wherein a rotating-unit-coupling part is provided on a first end of the elevating plate so that the elevating plate is coupled to the rotating shaft of the rotating unit by the rotating-unit-coupling part, and a sliding-plate-coupling part is provided on a second end of the elevating plate and has a coupling protrusion inserted into the sliding slot so that vertical movement of the sliding-plate-coupling part is guided by the coupling protrusion and the sliding slot.

6. The apparatus for manufacturing the multichannel electrode array for cranial nerve stimulation according to claim 5, wherein a semicircular shelf part is provided on a front end of the rotating-unit-coupling part such that the rotating shaft of the rotating unit is inserted into the semicircular shelf part, with a rotation indication member attached to the semicircular shelf part, the rotation indication member having protrusions on upper and lower ends thereof, and a plurality of indication depressions are formed in each of the upper and lower shaft flanges of the rotating unit at regular intervals so that the protrusions of the rotation indication member are inserted into the corresponding indication depressions.

7. The apparatus for manufacturing the multichannel electrode array for cranial nerve stimulation according to claim 4, wherein two left and right ones of the bobbins are disposed on the upper inner plate, and two front and rear ones of the bobbins are disposed on the upper outer plate, wherein when the manipulation units rotate, the upper inner plate rotates in a direction opposite to those of the outer plate and the lower plate, and the bobbins that have been disposed on the upper inner plate slide onto the upper outer plate, while the bobbins that have been disposed on the upper outer plate slide onto the upper inner plate.

8. The apparatus for manufacturing the multichannel electrode array for cranial nerve stimulation according to claim 1, wherein each of the manipulation units comprises:

a geared member coupled to the rotating unit;
a rotating shaft coupled to the geared member,
a sliding member coupled to the rotating shaft, the sliding member moving vertically along the vertical frame; and
a handle coupled to the rotating shaft.

9. The apparatus for manufacturing the multichannel electrode array for cranial nerve stimulation according to claim 8, wherein a gear is provided on the rotating shaft of each of the manipulation unit and is brought into contact with the vertical frame so that rotating force of the handle is transmitted to the vertical frame by the gear, thus sliding the sliding member.

* * * * *